United States Patent

Miyata et al.

Patent Number: 5,439,443
Date of Patent: Aug. 8, 1995

[54] BALLOON CATHETER

[75] Inventors: Shin'ichi Miyata; Tetsuo Toyokawa; Koichi Sakai, all of Yokohama; Hiroshi Hisaki, Yokosuka, all of Japan

[73] Assignee: Nippon Zeon Co., Ltd., Tokyo, Japan

[21] Appl. No.: 951,951

[22] Filed: Sep. 28, 1992

[30] Foreign Application Priority Data

Sep. 30, 1991 [JP] Japan ................ 3-278701
Sep. 30, 1991 [JP] Japan ................ 3-278702

[51] Int. Cl.⁶ .......................................... A61M 29/00
[52] U.S. Cl. ............................... 604/96; 606/194
[58] Field of Search ....................... 604/96–101; 606/191–194

[56] References Cited

U.S. PATENT DOCUMENTS

| | | | |
|---|---|---|---|
| 4,003,382 | 1/1977 | Dyke | 604/103 |
| 4,062,834 | 12/1977 | Gilding et al. | 623/1 |
| 4,490,421 | 12/1984 | Levy . | |
| 4,647,643 | 3/1987 | Zdrahala et al. | 528/28 |
| 4,743,673 | 5/1988 | Johnston et al. | 528/60 |
| 4,920,172 | 4/1990 | Daoud | 524/502 |
| 4,952,357 | 8/1990 | Euteneuer | 604/96 |
| 5,077,352 | 12/1991 | Elton | 525/409 |
| 5,100,992 | 3/1992 | Cohn et al. | 604/93 |
| 5,120,816 | 6/1992 | Gould et al. | 604/228 |
| 5,135,516 | 8/1992 | Sahatjian et al. | 604/266 |
| 5,179,174 | 1/1993 | Elton | 525/409 |
| 5,207,700 | 5/1993 | Euteneuer | 604/96 |

FOREIGN PATENT DOCUMENTS 0206255 8/1988 Japan .
63-206255 8/1988 Japan .
9001302 2/1990 WIPO .

OTHER PUBLICATIONS

Japanese Industrial Standard, "Test Method for Tensile Properties of Plastics", JIS K 7113–1981, Translated and published by Japanese Standards Association.
Japanese Industrial Standard, "Physical Testing Methods for Vulcanized Rubbber", JIS K 6301–1975, Translated and published by Japanese Standards Association.
Kenneth D. Stahl et al, "Intraaortic Balloon Rupture", vol. XXXIV Trans Am Soc. Artif Intern Organs, 1988.

Primary Examiner—C. Fred Rosenbaum
Assistant Examiner—Ronald K. Stright, Jr.
Attorney, Agent, or Firm—Lowe, Price, LeBlanc & Becker

[57] ABSTRACT

A balloon catheter having a balloon part composed of a film which is formed from a polymer having a number average molecular weight of at least 50,000, and has an initial modulus at 100% of at least 95 kg/cm² is provided. The balloon part is far excellent in preventive effect against its destruction is provided. The balloon catheter is suitable for use as a balloon catheter for intraaortic balloon pumping because the balloon part is prevented from being worn due to the rubbing of the balloon part against a calcified deposit on a blood vessel upon its practical operation.

1 Claim, 2 Drawing Sheets

BALLOON CATHETER

FIELD OF THE INVENTION

This invention relates to a balloon catheter, and more specifically to a balloon catheter which is suitable for use in intraaortic balloon pumping (IABP) and has a balloon part excellent in wear resistance.

BACKGROUND OF THE INVENTION

Intraaortic balloon pumping (IABP) has been recognized to have clinical assisting effects in the treatment for heart failure caused by myocardial infraction, or the like, and used worldwide. In IABP, a balloon attached to the tip of a catheter is synchronized with an electrocardiography and associated so as to deflate it at systole of a ventricle and inflate it at diastole of the ventricle, whereby a blood stream in a coronary artery is increased at diastole to reduce ischemia and hence heart failure is improved, and the resistance of the blood stream is reduced at systole and the load of a left ventricle is hence relieved.

A balloon catheter used in IABP is inserted through a femoral artery, and the tip thereof is positioned in the descending aorta of a thoracic part right under the bifurcation of a left subclavian artery. The portion of the balloon catheter out of the body is connected to an IABP apparatus including a pumping system. The inflation and deflation of the balloon is conducted by pumping. Helium or carbon dioxide is used as an operation gas. As normal materials of the balloon part, have been used films formed of various polymeric materials such as polyurethane, polyurethane urea, polyurethane-silicone block copolymers, fluorinated polyurethane, fluorinated polyurethane urea and polymerblends of polyurethane and polydimethylsiloxane.

As described above, IABP has been recognized to have advantageous effects over both diastole and systole and hence is an excellent means as an assisted circulation. However, some side effects have been reported as its clinical application range has extended. As an example thereof, there is an "Intraaortic Balloon Rupture" reported by Kenneth D. Stahl et al., American Society Artificial Internal Organs, Vol. 34 (1988). A particularly grave side effect is to destroy (rupture, damage) the balloon. In the above report, the trouble due to such destruction has been reported to be 2.4% of all cases. The destruction of the balloon part brings not only loss in the effect of assisted circulation on a patient, but also discharging of helium or carbon dioxide as an operation gas into the blood vessel of the patient, resulting in grave side effects such as embolism.

As a protective measure for avoiding such a serious situation, a function to output an alarm signal when the discharging of the operation gas reaches a certain amount or more is incorporated into most of commercially available IABP apparatus. However, it has been known that the operation gas dissolves in the blood least by least due to its diffusion even when the balloon does not leak a gas, and is lost gradually. Therefore, if an alarming mechanism is designed to detect the loss of gas sharply and microscopically, it is difficult to distinguish the loss due to the diffusion from the loss caused by the trouble of the balloon. It is hence impossible to detect the trouble of the balloon in its early stage.

On the other hand, it has been proposed to form balloon parts in sizes and shapes fit for the body build of Japanese and from materials high in thrombus resistance and excellent in mechanical strength with respect to balloon catheters used in IABP (Japanese Patent Application Laid-Open No. 206255/1988). It is desirable to regulate the maximum diameter and length of the balloon parts according to the shapes of the blood vessels of patients and/or the like from the viewpoint of the effect of assisted circulation and the prevention of destruction of the balloon part. However, since the shapes of the blood vessels of the patients greatly vary due to individual difference, the patient's share in expense and doctor's trouble become greater because the sizes of the blood vessels of the individual patients must be measured precisely and the balloon parts must be formed according to such sizes. In addition, the forming operation of the balloon catheters also becomes complicated. Besides, if the volume of the balloon part is made too small with paramount consideration for patient's safety, the effect of assisted circulation owing to IABP is reduced. Further, the conventional materials by which the balloon parts are formed are insufficient in preventive effect against the destruction of the balloon.

OBJECTS AND SUMMARY OF THE INVENTION

It is an object of this invention to provide a balloon catheter having a balloon part far excellent in preventive effect against its destruction.

The present inventors have carried out an investigation on the destruction of balloon catheters. As a result, it has been found that when a balloon catheter is operated in an aorta, a balloon part is rubbed against a calcified deposit present in the aorta, whereby the wear of the balloon part is allowed to progress from its outer surface, which forms the main cause of the destruction of the balloon part.

Namely, the present inventors have observed the surfaces of balloon parts of balloon catheters for IABP, said balloon parts being made of polyurethane and having been destroyed due to clinical use, and the sections of the destroyed parts and their surrounding areas through a scanning electron microscope. As a result, it has been confirmed that the thickness of each of the balloons was rendered thin, thereby causing its destruction. It can be considered that such thinning of the balloon thickness is caused by its wear. Specifically, it can be inferred that upon repeated inflation and deflation of the balloon while the balloon catheter is being used, the balloon is rubbed against the calcified deposit on the inner wall of the blood vessel, so that the wear of the balloon part is allowed to progress from its outer surface.

In order to confirm this fact, the following wearing test was conducted using a rub tester equipped with a roll illustrated in FIGS. 1 and 2 and made from plaster. After the same polyurethane film as that used in the formation of the balloons was rubbed against the roll under the same conditions of pressure and tension as those in the operation of a balloon catheter, the surface and section of the film was observed through a scanning electron microscope. As a result, it has been found that wear similar to that in the clinically destroyed balloons is caused.

As described above, the destruction of the balloon part of the balloon catheter is presumed to be caused by the wear due to the rubbing of the balloon part against the calcified deposit on the inner wall of the blood vessel. It is therefore necessary to form a balloon from a material excelling in wear resistance against the calcified deposit in order to prevent its destruction. Namely, since the wear of a film presents complex phenomenons according to various conditions under which the film is held, the improvement in wear resistance requires solutional measures suited to specific wear conditions.

Therefore, a wearing test was conducted on various films by the wear tester so as to provide materials for balloons excellent in wear resistance. As a result, it has been found that a film which is formed from a polymer having a number average molecular weight of 50,000 or higher, and has an initial modulus at 100% of 95 kg/cm$^2$ or higher exhibits remarkable wear resistance, and is suitable for use as a material for forming balloon parts hard to be destroyed in clinical use.

The present invention has been led to completion on the basis of these findings.

According to the present invention, there is thus provided a balloon catheter having a balloon part composed of a film which is formed from a polymer having a number average molecular weight of at least 50,000, and has an initial modulus at 100% of at least 95 kg/cm$^2$.

DETAILED DESCRIPTION OF THE INVENTION

Figure 1:
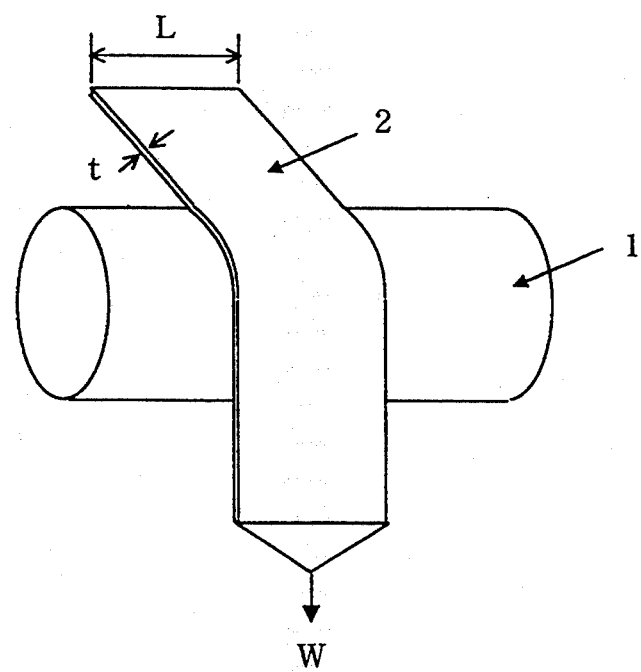
FIG. 1 is a schematic drawing illustrating a wear tester used in this invention and how to use such a tester.

The present invention will hereinafter be described in detail.

In the balloon catheter according to this invention, no particular limitation is imposed on the kind of a polymer from which a balloon part is formed. Various polymers known as materials for balloons, for example, polyurethane, polyurethane urea, polyurethane-silicone block copolymers, fluorinated polyurethane, fluorinated polyurethane urea and the like, may be used suitably. These polymers may be blends with a polymer of a different kind like a polyblend of polyurethane and polydimethylsiloxane, or with a polymer of the same kind.

As examples of the polyurethane (or the polyurethane ureas), may be mentioned polyurethanes comprising, as a hard segment, urethane or urea bonds composed of a diisocyanate such as 4,4'-diphenylmethane diisocyanate (MDI), hydrogenated MDI or hexamethylene diisocyanate and a short-chain diol such as 1,4-butanediol or ethylene glycol, and as a soft segment, polyethers such as polyoxytetramethylene glycol or polyoxypropylene glycol, adipic esters such as ethylene adipate or butylene adipate, or aliphatic polyesters such as polycaprolactone or polycarbonate.

Accordingly, as an isocyanate compound constituting the hard segment in the polyurethane, may be used various polyisocyanate including the above-mentioned MDI. Also, as a polyol compound constituting the soft segment, may be used polyether polyols such as polyoxytetramethylene glycol (PTMG) and polyoxypropylene glycol (PPG); polyester polyols such as condensed polyester polyols, for example, ethylene adipate and butylene adipate, and lactone type polyester polyols obtained by the ring opening polymerization of ε-caprolactone; polycarbonate polyols; and the like. As a chain extender, may be used short-chain diols such as 1,4-butanediol and ethylene glycol, and diamines such as ethylenediamine. Polyurethanes composed of these components include thermoplastic polyurethane elastomers.

When a diisocyanate having a fluorine-containing group such as perfluoroalkylene group is used, fluorine-containing polyurethanes can be obtained. Composite polyurethanes composed of a polyether polyurethane and a polydimethylsiloxane polymer, and MDI, PTMG, EO-polydimethylsiloxane block copolymers (EO=ethylene oxide) may also be used.

In the present invention, it is essential to use, as a material for the balloon, a polymer having an number average molecular weight (Mn) of at least 50,000. In this invention, the number average molecular weight (Mn) of each polymer means a value determined by the gel permeation chromatography (GPC) method.

All the number average molecular weights of the polymers which are commercially available at present and used for forming a balloon part are lower than 50,000. Any polymers having a number average molecular weight lower than 50,000 result in a balloon part significantly lowered in wear resistance. The number average molecular weight is preferably not lower than 60,000, more preferably not lower than 80,000. No particular limitation is imposed on the upper limit of the number average molecular weight. However, it is desirable to control it to, generally, not higher than 150,000, preferably, not higher than 130,000 from the viewpoint of the solubility in solvent in a film-forming process and the easiness of synthesis.

However, as will be described subsequently, a balloon may be formed by a crosslinked film obtained by forming a polyurethane type polymer into a film having a desired shape and then crosslinking the film to give a gel content of at least 40 wt. %. In this case, the number average molecular weight of the polyurethane type polymer as a raw material is not necessarily at least 50,000. In such a crosslinked film, the number average molecular weight can not be determined by the GPC method because the polyurethane type polymer is hard to dissolve in a solvent due to its crosslinking. However, such a crosslinked polymer may also be estimated to have a number average molecular weight of 50,000 or higher.

It is essential for the polymer used in forming the balloon part according to this invention to have an initial modulus at 100% of at least 95 kg/cm$^2$ as measured in the form of a film. Any initial modulus at 100% lower than 95 kg/cm$^2$ result in a balloon part insufficient in wear resistance even if the number average molecular weight of the polymer is 50,000 or higher. The initial modulus at 100% of the film is preferably at least 100 kg/cm$^2$, more preferably at least 110 kg/cm$^2$. No particular limitation is imposed on the upper limit of the initial modulus. However, it is generally not higher than 200 kg/cm$^2$ in view of the easiness of synthesis, and the like.

In the present invention, the initial modulus at 100% is a value as measured in accordance with JIS K-6301. The term "initial" means that the modulus at 100% is calculated in accordance with the method of calculation as to the modulus in tension in JIS K-7113 using an initial straight part of a stress-strain curve.

The polymer used in this invention can be synthesized in accordance with the various polymerization processes. For example, the polyurethane may be synthesized by the prepolymer process, one-shot process or other process.

In this case, in order to control the number average molecular weight and initial modulus at 100% of the polyurethane to desired values, the synthesis may be conducted, for example, by varying the proportion of the hard segment to the soft segment.

Although various film-forming process may be used to form balloons with these polymers, dip forming is usually preferred in the case of the polyurethane type polymer.

In the dip forming, a polymer is dissolved in an organic solvent into a solution. A form is then dipped into the solution. Namely, the form is dipped into a polymer solution to apply the polymer solution on the surface of the form. The solvent is then evaporated to form a polymer film on the surface of the form. The dipping and drying are conducted repeatedly, whereby a laminated film having a desired thickness can be formed. By this forming process, a balloon of a bag-like structure which is cylindrical and tapered at both ends is formed. As examples of the solvent, may be mentioned various organic solvents such as tetrahydrofuran, dimethylformamide, dimethylacetamide, N-methyl-2-pyrrolidone and dimethyl sulfoxide.

In the case where a balloon is produced in accordance with the dip forming, it is desirable that the gel content in the polymer should be as low as possible in order to give a film even in thickness. If the gel content in the polymer is too high, the resulting film becomes uneven in thickness, whereby the film undergoes stress concentration, resulting in fatigue failure. Alternatively, irregularities are formed on the surface of the film and may accelerate the formation of thrombus when the balloon is used in the blood. From such points of view, the polymer used in this invention desirably has a gel content of, usually, 30 wt. % or lower, preferably, 10 wt. % or lower, more preferably, 5 wt. % or lower.

In this invention, the gel content in the polymer is a value obtained by the following measuring method. About 5 g of a polymer is weighed precisely and placed on a 400-mesh screen. The screen is softly immersed in 100 ml of tetrahydrofuran or dimethylformamide and then left over for 24 hours at room temperature. Thereafter, the screen is softly drawn up. After the undissolved gel remaining on the screen is thoroughly dried, the weight of the gel is measured to calculate the weight fraction of the gel to the weight of the original polymer.

As described above, the dip forming in which a form is dipped into a polymer solution, and a film is formed on the surface of a mold is principally used in order to form a balloon part from a polymer. In this process, the solubility of the polymer in an organic solvent is important. For example, a polymer high in molecular weight or gel content is low in solubility, and is hence poor in formability and processability.

Therefore, the present inventors have carried out a further investigation. As a result, it has been found that when a polyurethane type polymer is formed into a film having a desired shape and then crosslinked to give a gel content of at least 40 wt. %, a film-forming process can be performed without impairing formability and processability. In addition, the resulting crosslinked film is high in molecular weight and initial modulus at 100% owing to its crosslinking. Further, a balloon part formed of the crosslinked film exhibits remarkable wear resistance, so that a balloon catheter hard to be destroyed in clinical use can be provided.

The crosslinking process for the polyurethane type polymer includes a variety of crosslinking processes such as allophanate crosslinking and biuret crosslinking. The crosslinking is usually conducted at the time the polymer is formed. In this invention, the crosslinking is however conducted after the polyurethane type polymer is formed into a film having a desired shape.

In order to crosslink the polyurethane type polymer after the formation of a film having a desired shape, there is, for example, a process in which an incomplete polyurethane containing residual active isocyanate groups on terminals of its molecular chain and in the molecular chain is used. The incomplete polyurethane can be obtained by charging a diisocyanate to constitute the hard segment of the polyurethane in a stoichiometrically excessive amount to a polyol compound and polymerizing them. When this incomplete polyurethane is used to form it into a film having a desired balloon shape, and the resulting film is heated, the incomplete polyurethane undergoes allophanate crosslinking due to the residual isocyanate groups. The heat treatment for the crosslinking is usually conducted by heating the film for several tens of minutes to several hours at 80°–150° C.

With respect to other polyurethane type polymers such as polyurethane urea and fluorinated polyurethane, incomplete polyurethanes containing residual isocyanate groups can also be prepared in the same manner as described above. Therefore, the term "incomplete polyurethane" as used in this invention means including a variety of these polyurethane type polymers containing residual isocyanate groups.

As another crosslinking process, may be mentioned a process in which crosslinking is conducted by using a monomolecular polyisocyanate. In the crosslinking of formed or molded products of polyurethane type polymers, there has been known, for example, a process in which a polyisocyanate such as a diisocyanate is added to a thermoplastic polyurethane elastomer to crosslink the elastomer. In this invention, a polyurethane type polymer is formed into a film having a desired shape and then immersed in a solvent containing a polyisocyanate, followed by crosslinking under heat.

For example, a film formed in a desired shape is immersed in a solution of 4,4'-diphenylmethane diisocyanate in tetrahydrofuran for several seconds to several tens of seconds and then taken out of the solution. The thus-treated film is then heated for several tens of minutes to several hours at 80°–150° C., thereby undergoing allophanate crosslinking and/or biuret crosslinking. A crosslinked film can thus be obtained.

As raw polyurethane type polymers useful in the formation of the crosslinked film, may be used not only polymers having a number average molecular weight (Mn) of 50,000 or higher, but also lower-molecular weight polymers.

The crosslinked film obtained by forming the polyurethane type polymer into the film in the desired shape and then crosslinking the formed film must have a gel content of at least 40 wt. %. Any gel contents lower than 40 wt. % result in a crosslinked film too low in crosslinking degree to achieve a sufficient effect to improve the wear resistance. The gel content in the crosslinked film is preferably at least 45 wt. %. Incidentally, the crosslinked film according to this invention has a smooth surface even when its gel content is high because the crosslinking is conducted after the formation of the film.

The crosslinked film has an initial modulus at 100% of at least 95 kg/cm$^2$, preferably at least 100 kg/cm$^2$, more preferably at least 110 kg/cm². If the initial modulus at 100% is lower than 95 kg/cm², the wear resistance of the film tends to be insufficient even though the crosslinking treatment is conducted. No particular limitation is imposed on the upper limit of the initial modulus at 100%.. However, it is generally not higher than 200 kg/cm².

The thickness of the balloon part in the balloon catheter according to this invention may be suitably determined as desired. It is however desirable to control the thickness to an extent of, generally, 0.03–1.00 mm, preferably, 0.05–0.50 mm, more preferably, 0.08–0.20 mm in order to achieve sufficient mechanical strength, wear resistance and operatability.

ADVANTAGES OF THE INVENTION

According to the present invention, a balloon catheter having a balloon part far excellent in preventive effect against its destruction is provided. The balloon catheter according to this invention is suitable for use as a balloon catheter for intraaortic balloon pumping because its balloon part is prevented from being worn due to the rubbing of the balloon part against a calcified deposit on a blood vessel upon its practical operation.

EMBODIMENTS OF THE INVENTION

The present invention will hereinafter be described specifically by the following examples and comparative examples. It should however be borne in mind that this invention is not limited to the following examples only.

Incidentally, the following methods were followed for the measurement of the physical properties in the following examples.

Number Average Molecular Weight (Mn)

Determined by the GPC method. Measuring conditions are as follows:
Column: A-80M and A-802 (manufactured by Showa Denko K.K.), two A-80M columns and one A-802 column in series
Solvent: tetrahydrofuran
Flow rate: 1.2 ml/min
Temperature: 40.0° C.
Sample concentration: 0.5 wt. %
Charged amount: 200 μl
Detector: UV, 254 nm
Calibration of molecular weight: standard polyethylene
Data processing: TRI ROTOR-V (manufactured by Japan Spectroscopic Co., Ltd.)

Initial Modulus at 100%

Measured in accordance with JIS K-6301.

Loss in Weight

Figure 2:
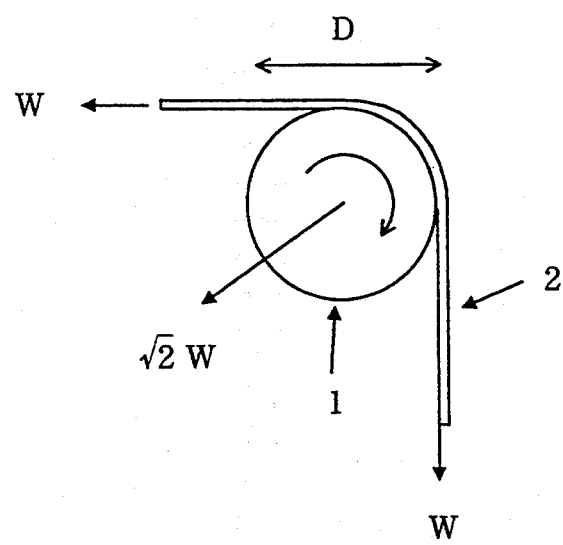
FIG. 2 is a schematic sectional view of the wear tester shown in FIG. 1.

With respect to a film formed from each polymer, a wearing test was conducted with a wear tester illustrated in FIGS. 1 and 2, followed by determination of loss in weight.

In FIGS. 1 and 2, a plaster roll 1 was formed by grinding a block of plaster into the form of a roll by a lathe and then rubbing the surface of the roll-like plaster with sand paper, No. 400, to smoothly finish it, and had a diameter D of 1.6 cm or 0.8 cm and a length of 10 cm. The diameter was selected according to the thickness of a film to be tested to control the conditions of tension and pressure.

A sample film 2 was placed on the plaster roll 1 in a manner illustrated in FIGS. 1 and 2. One end of the film 2 was weighed, and the other end was fixed.

Suppose W, A and S are a load (kg) of a weight, a sectional area (width $L \times$ thickness t of the film, cm²) of the film and a contact area (width $L \times \pi/4 \times D$, cm²) between the roll and the film, respectively, the tension T and pressure P applied to the film can be determined in accordance with the following equations:

$T = W/A$ (kg/cm²)

$P = \sqrt{2}W/S$ (kg/cm²)

Under the conditions of 7 kg/cm² in tension T and 0.2 kg/cm² in pressure P, the plaster roll 1 was rotated on its own axis at a rotational speed of 21 cm/sec until the film was cut. In this invention, these conditions as to the tension and pressure were preset so as to be substantially the same as the force exerted on a balloon at the last stage of inflation of the balloon upon the practical operation of a balloon catheter.

After completion of the wearing test, the abrasion loss of the film was determined to calculate the loss in weight per unit contact area and unit time (mg/cm²·min).

Gel Content

About 5 g of polymer is weighed precisely and placed on a 400-mesh screen. The screen is softly immersed in 100 ml of a solvent such as tetrahydrofuran and left over for 24 hours at room temperature. Thereafter, the screen is softly drawn up. After the undissolved gel remaining on the screen is thoroughly dried, the weight of the gel is measured, thereby calculating the weight fraction of the gel to the weight of the original polymer.

EXAMPLE 1

Various polyurethanes of polyether (Ether), polyester (Ester), caprolactone (Capro) and polycarbonate (Carbon) types were synthesized by suitably using the following materials.

Materials for Polyurethanes

Polyisocyanate 4,4'-Diphenylmethane diisocyanate (MDI)

Polyols (1) Polytetramethylene ether glycol (TMG), weight average molecular weight (Mw)=650 (product of Hodogaya Chemical Co., Ltd.)
(2) Polypropylene ether glycol (PPG), weight average molecular weight (Mw)=250 (product of Bayer AG, Germany)
(3) Polyethylene adipate (AD), weight average molecular weight (Mw)=500 (product of Bayer AG, Germany)
(4) Polyester caprolactonediol (CPL), weight average molecular weight (Mw)=550 (product of UCC Corp., U.S.A.)
(5) Polycarbonatediol (CBN) weight average molecular weight (Mw)=250 (product of Permanol Co., U.S.A. )

Chain Extender 1,4-Butanediol

Synthesis of polyurethane

A reactor equipped with a stirrer, a reflux condenser and a nitrogen gas inlet and dried thoroughly were charged with MDI (10.0 g, 40 mM) and corresponding polyol(s) (20 mM) and 100 ml of dimethyl sulfoxide (DMSO). The contents were rapidly heated to about 50° C. under a nitrogen gas atmosphere to react them for 3 hours. Incidentally, all the polyols were dried under reduced pressure and further dewatered with molecular sieves before their use.

The reaction mixture was then cooled to room temperature and added with 20 mM of 1,4-butanediol. The mixture was stirred for 1 hour.

The resultant reaction mixture was poured in a great amount of water to precipitate a polymer formed. The polymer was washed several times over with water and then ground by a Waring blender. The thus-ground polymer was dried in an air oven of 80° C.

The thus-obtained polyurethanes were subjected to component analysis on the basis of the $^1$H-NMR measurement. The results are shown in Table 1.

For the sake of comparison, the compositions of commercially available polyurethane-made balloons (products of A, D and M companies) used in IABP are also shown in Table 1.

Film-forming Process

Each of the polyurethanes obtained in the above-described manner was dissolved in tetrahydrofuran or dimethylformamide. After the resulting solution was coated on a glass sheet, the solution was dried in a sealed vessel while controlling the evaporation speed of the solvent by ventilating only a part of the sealed vessel, thereby forming a film. The thus-obtained film was further left over for 12 hours at 65° C. and then cooled in air.

The physical properties of the films thus obtained were measured. These films were also subjected to a wearing test with the above-described rub tester to determine their loss in weight.

The measurement results as to the physical properties, thickness and loss in weight of the individual films are shown collectively in Table 2.

TABLE 1

| Polymer code No. | Type | MDI | TMG | PPG | AD | CPL | CBN |
|---|---|---|---|---|---|---|---|
| A | Ether | 1 | 4.5 | 1.5 | | | |
| D | Ester | 1 | 2.5 | | 1.7 | | |
| M | Ester | 1 | 3.4 | | 2.0 | | |
| 1 | Ether | 1 | 4.3 | 0.4 | | | |
| 2 | Ether | 1 | 5.3 | | | | |
| 3 | Ether | 1 | 5.7 | | | | |
| 4 | Ether | 1 | 4.2 | | | | |
| 5 | Ether | 1 | 5.8 | | | | |
| 6 | Ether | 1 | 6.0 | | | | |
| 7 | Ether | 1 | 5.9 | | | | |
| 8 | Ester | 1 | 2.5 | | 1.4 | | |
| 9 | Ester | 1 | 3.6 | | 3.3 | | |
| 10 | Ester | 1 | 3.8 | | 2.8 | | |
| 11 | Ester | 1 | 3.2 | | 2.2 | | |
| 12 | Ester | 1 | 2.6 | | 1.6 | | |
| 13 | Ester | 1 | 3.3 | | 2.2 | | |
| 14 | Capro | 1 | 0.7 | | | 5.1 | |
| 15 | Capro | 1 | 0.7 | | | 5.0 | |
| 16 | Capro | 1 | 1.1 | | | 4.2 | |
| 17 | Capro | 1 | 1.1 | | | 2.7 | |
| 18 | Capro | 1 | 1.1 | | | 2.1 | |
| 19 | Capro | 1 | 1.0 | | | 3.2 | |
| 20 | Capro | 1 | 1.1 | | | 4.9 | |
| 21 | Carbon | 1 | 0.6 | | | | 4.5 |

TABLE 2

| Expt. No. | Polymer code No. | Type | Mn | Film thickness mm | Modulus at 100% kg/cm$^2$ | Loss in weight mg/cm$^2$ · min | Remarks |
|---|---|---|---|---|---|---|---|
| I-1 | 9 | Ester | 33,000 | 0.25 | 48 | 1.026 | Comp. Ex. |
| I-2 | 16 | Capro | 49,000 | 0.25 | 77 | 0.831 | |
| I-3 | 13 | Ester | 44,500 | 0.23 | 89 | 0.766 | |
| II-1 | A | Ether | 25,000 | 0.11 | 99 | 0.900 | Comp. Ex. |
| II-2 | 1 | Ether | 28,000 | 0.25 | 99 | 1.188 | |
| II-3 | 7 | Ether | 49,500 | 0.21 | 101 | 0.614 | |
| II-4 | D | Ester | 48,000 | 0.10 | 130 | 0.690 | |
| II-5 | 8 | Ester | 47,000 | 0.22 | 135 | 0.542 | |
| II-6 | M | Ester | 47,000 | 0.12 | 135 | 0.703 | |
| III-1 | 10 | Ester | 60,000 | 0.25 | 42 | 1.223 | Comp. Ex. |
| III-2 | 13 | Capro | 63,000 | 0.25 | 48 | 0.920 | |
| III-3 | 14 | Capro | 92,000 | 0.26 | 54 | 0.551 | |
| III-4 | 3 | Ether | 70,000 | 0.25 | 62 | 0.701 | |
| III-5 | 20 | Capro | 81,000 | 0.24 | 66 | 0.829 | |
| III-6 | 11 | Ester | 77,000 | 0.26 | 82 | 0.555 | |
| III-7 | 18 | Capro | 89,500 | 0.25 | 85 | 0.511 | |
| III-8 | 21 | Carbon | 80,000 | 0.25 | 86 | 0.555 | |
| III-9 | 5 | Ether | 50,000 | 0.29 | 90 | 0.765 | |
| III-10 | 6 | Ether | 50,000 | 0.24 | 92 | 0.564 | |
| IV-1 | 2 | Ether | 104,000 | 0.22 | 98 | 0.416 | Example |
| IV-2 | 17 | Capro | 50,000 | 0.24 | 115 | 0.345 | |
| IV-3 | 19 | Capro | 80,000 | 0.27 | 117 | 0.346 | |
| IV-4 | 12 | Ester | 68,500 | 0.25 | 128 | 0.305 | |
| IV-5 | 4 | Ether | 108,000 | 0.29 | 175 | 0.169 | |

In Table 2, the polyurethanes (including commercially available products) having their corresponding compositions shown in Table 1 were shown by classifying into four groups of (1) a group (Group I) in which Mn of the polymers are lower than 50,000 and the initial modulus at 100% of the films are lower than 95 kg/cm$^2$, (2) a group (Group II) in which Mn of the polymers are lower than 50,000, but the initial modulus at 100% of the films are not lower than 95 kg/cm$^2$, (3) a group (Group III) in which Mn of the polymers are not lower than 50,000, but the initial modulus at 100% of the films are lower than 95 kg/cm$^2$, and (4) a group (Group IV) according to an embodiment of this invention, in which Mn of the polymers are not lower than 50,000, and the initial modulus at 100% of the films are also not lower than 95 kg/cm$^2$.

As apparent from Table 2, it is understood that the kinds of polyol and the presence of polyester bonds make no difference in the wear resistance of the films, and the wear resistance is remarkably improved for the first time where both Mn and initial modulus at 100% meet the requirements defined by this invention.

EXAMPLE 2

Synthesis Experiments of Polyurethanes

Synthesis Experiment 1

A reactor equipped with a stirrer, a reflux condenser and a nitrogen gas inlet and dried thoroughly were charged with MDI (10.0 g, 40 mM), a mixed polyol (20 mM) of TMG and PPG and 100 ml of DMSO. The contents were rapidly heated to about 50° C. under a nitrogen gas atmosphere to react them for 3 hours. Incidentally, all the polyols were dried under reduced pressure and further dewatered with molecular sieves before their use. The reaction mixture was then cooled to room temperature and added with 20 mM of 1,4-butanediol. The resulting mixture was stirred for 1 hour. The resultant reaction mixture was poured in a great amount of water to precipitate a polymer formed. The polymer was washed several times over with water and then ground by a Waring blender. The thus-ground polymer was dried in an air oven of 80° C., thereby obtaining Polyurethane No. 22. Polyurethane No. 22 is identical to Polymer No. 1 in Example 1.

Synthesis Experiment 2

Incomplete Polyurethane No. 23 was obtained in the same manner as in Synthesis Experiment 1 except that the molar ratio of MDI was raised by 10%. Incomplete Polyurethane No. 23 corresponds to Polyurethane No. 22 except that the incomplete polyurethane contained residual active isocyanate groups in its molecule.

Synthesis Experiment 3

Polyurethane No. 24 was obtained in the same manner as in Synthesis Experiment 1 except that a mixed polyol of TMG and AD was used as a polyol. Polyurethane No. 24 is identical to Polymer No. 10 in Example 1.

Synthesis Experiment 4

Incomplete Polyurethane No. 25 was obtained in the same manner as in Synthesis Experiment 3 except that the molar ratio of MDI was raised by 10%. Incomplete Polyurethane No. 25 corresponds to Polyurethane No. 24 except that the incomplete polyurethane contained residual active isocyanate groups in its molecule.

Polyurethanes obtained in Synthesis Experiments 1–4 were separately dissolved in tetrahydrofuran. A form in the shape of a balloon is dipped into each of the resulting solutions. Balloon films were then formed in the same manner as in Example 1.

The balloons (films) obtained by using Incomplete Polyurethane Nos. 23 and 25 were heated for 1 hour at 85° C. to crosslink them.

With respect to the balloons (films) thus obtained, the physical properties were measured. For the sake of comparison, the physical properties of the commercially available products A and M were also measured.

The measurement results are shown collectively in Table 3.

TABLE 3

| Experiment No. | polymer code No. | Crosslinking | Gel content wt. % | Mn | Film thickness mm | Modulus at 100% kg/cm$^2$ | Loss in weight mg/cm$^2$ · min | Remarks |
| --- | --- | --- | --- | --- | --- | --- | --- | --- |
| 2-1 | 22 | Not conducted | 0.1 | 28,000 | 0.25 | 99 | 1.188 | Comp. Ex. |
| 2-2 | 23 | Conducted | 72.8 | Unmeasurable | 0.25 | 138 | 0.305 | Example |
| 2-3 | 24 | Not conducted | 0.4 | 60,000 | 0.25 | 42 | 1.223 | Comp. Ex. |
| 2-4 | 25 | Conducted | 40.2 | Unmeasurable | 0.25 | 97 | 0.416 | Example |
| 2-5 | A | Not conducted | 0.2 | 25,000 | 0.11 | 99 | 0.900 | Comp. Ex. |
| 2-6 | M | Not conducted | 0.4 | 47,000 | 0.12 | 135 | 0.703 | Comp. Ex. |

As apparent from Table 3, it is understood that the crosslinked films (Experiment Nos. 2-2 and 2-4) according to an embodiment of this invention, which have been separately obtained by forming a film with the corresponding incomplete polyurethane and then crosslinking the film under heat, exhibit excellent wear resistance. By the way, the number average molecular weights of these crosslinked films were unmeasurable by GPC because they contained insoluble matter in the solvent in a great proportion. Therefore, the number average molecular weights of these crosslinked films are undoubtedly 50,000 or higher.

EXAMPLE 3

A balloon was formed in the same manner as in Example 1 except that Polyurethane No. 22 obtained in Synthesis Experiment 1 of Example 2 was used.

The resulting balloon (film) was immersed for 5 seconds or 30 seconds in a solution (concentration: 4 wt. %) of 4,4'-diphenylmethane diisocyanate (MDI) in tetrahydrofuran (THF), and then heated for 2 hours at 105° C., thereby crosslinking the film.

The physical properties of the uncrosslinked film and crosslinked films are shown in Table 4.

TABLE 4

| Experiment No. | polymer code No. | Crosslinking | Gel content wt. % | Mn | Film thickness mm | Modulus at 100% kg/cm$^2$ | Loss in weight mg/cm$^2$ · min | Remarks |
| --- | --- | --- | --- | --- | --- | --- | --- | --- |
| 3-1 | 22 | Not conducted | 0.1 | 28,000 | 0.25 | 99 | 1.118 | Comp. Ex. |
| 3-2 | 22 | Conducted*1 | 46.5 | Unmeasurable | 0.25 | 115 | 0.398 | Example |
| 3-3 | 22 | Conducted*2 | 69.5 | Unmeasur- | 0.25 | 128 | 0.331 | Example |

TABLE 4-continued

| Experiment No. | polymer code No. | Crosslinking | Gel content wt. % | Mn | Film thickness mm | Modulus at 100% kg/cm² | Loss in weight mg/cm²·min | Remarks |
|---|---|---|---|---|---|---|---|---|
| | | | | able | | | | |

*¹Crosslinked under heat after immersed for 5 seconds in the solution of MDI in THF.
*²Crosslinked under heat after immersed for 30 seconds in the solution of MDI in THF.

As apparent from Table 4, it is understood that the crosslinked films (Experiment Nos. 3-2 and 3-3) have excellent wear resistance. By the way, the number average molecular weights of these crosslinked films were unmeasurable by GPC because they contained insoluble matter in the solvent in a great proportion. Therefore, the number average molecular weights of these crosslinked films are undoubtedly 50,000 or higher.

We claim:

1. In a balloon catheter comprising a catheter and a balloon part attached to the tip of the catheter, the improvement wherein the balloon part is composed of an uncrosslinked film which is formed from at least one polyurethane type polymer selected from the group consisting of polyurethane, polyurethane urea, and polyurethane-silicon block copolymers and having a number average molecular weight of at least 50,000 and an initial tensile modulus at 100% of at least 95 kg/cm².

* * * * *